United States Patent [19]

Kwan et al.

[11] Patent Number: 5,178,874
[45] Date of Patent: Jan. 12, 1993

[54] INTERMITTENT RELEASE DOSAGE FORM

[75] Inventors: Lilian Kwan, Saint Davids, Pa.; William Steber, Ledgewood, N.J.

[73] Assignee: SmithKline Beechman Corporation, Philadelphia, Pa.

[21] Appl. No.: 858,911

[22] Filed: Mar. 27, 1992

Related U.S. Application Data

[63] Continuation of Ser. No. 617,476, Nov. 20, 1990, Pat. No. 5,110,598.

[51] Int. Cl.⁵ .............................................. A23K 1/18
[52] U.S. Cl. ........................... 424/438; 424/475; 427/3
[58] Field of Search .................. 424/438, 475, 480; 427/3

[56] References Cited

U.S. PATENT DOCUMENTS

| | | | |
|---|---|---|---|
| 3,507,952 | 4/1970 | Rednick | 424/22 |
| 4,479,911 | 10/1984 | Fong | 427/3 |
| 4,564,363 | 1/1986 | Bagnall | 604/891 |
| 4,642,230 | 2/1987 | Whitehead | 424/15 |

FOREIGN PATENT DOCUMENTS 0164927 12/1985 European Pat. Off. .

Primary Examiner—Thurman K. Page
Assistant Examiner—D. Gabrielle Phelan
Attorney, Agent, or Firm—Dara L. Dinner; Stephen Venetianer; Edward T. Lentz

[57] ABSTRACT

Veterinary delayed release dosage forms which remain in the rumeno-reticular sac of an animal over an extended period of time and in which the therapeutically active substance has a predictable and delayed release pattern. The compositions comprise a dense filler, a disintegrant and a therapeutically active substance. The dosage form has a hydrophobic polymer or co-polymer coating and can deliver a plurality of doses of a medicament intermittently at a preset time interval in the rumen.

7 Claims, 3 Drawing Sheets

FIG 9
FIG 10
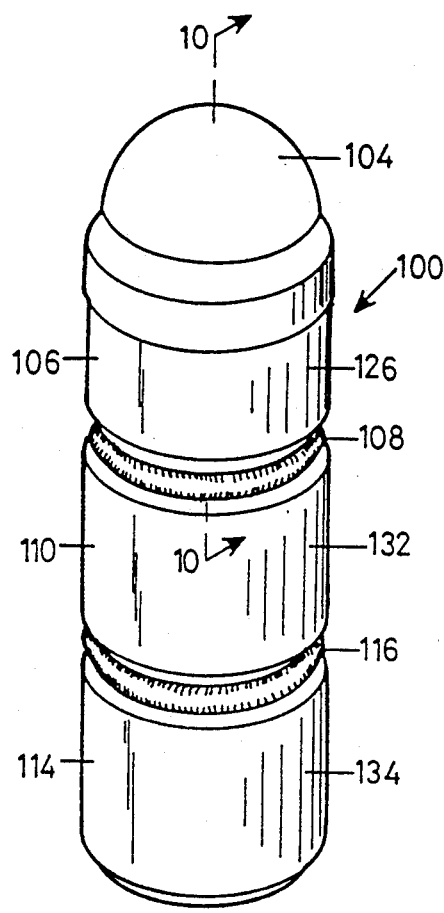
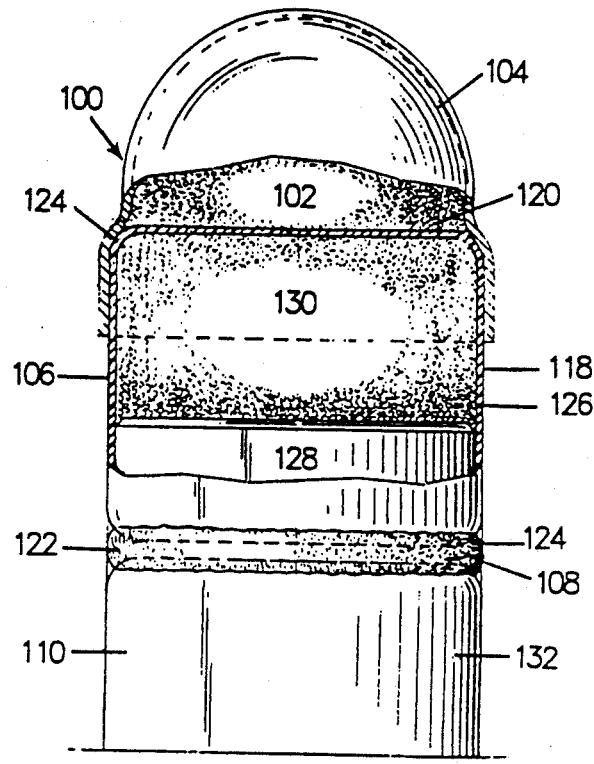
FIG 11
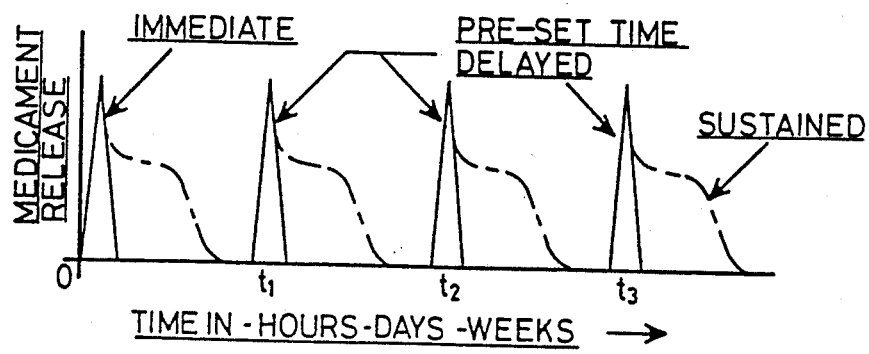

INTERMITTENT RELEASE DOSAGE FORM

This is a continuation of application Ser. No. 07/617,476 filed Nov. 20, 1991, now U.S. Pat. No. 5,110,598.

This Invention relates to veterinary delayed release dosage forms, particular for the administration of therapeutic substances to ruminants such as cattle and sheep. More specifically- this invention relates to bolus like dosage forms intended to remain in the rumeno-reticular sac of an animal over an extended period of time.

BACKGROUND OF THE INVENTION

In the veterinary field, the use of sustained release dosage forms of medication which remain in the rumeno reticular sac for a prolonged period of time is well known. These dosage forms are usually in the form of boluses and are dense and heavy enough to stop in the rumeno reticular sac and remain there rather than pass into the alimentary tract and be eliminated intact. The physical form of these dosage forms is retained over a long period of time in the sac while the therapeutically active substance is slowly released by erosive or solubilization action within the sac. In other words, regardless of the therapeutically active substance to be administered, the bolus itself must comply with the physical requirements as to density weight. In order to meet the proper requirements for density and weight, iron, sand or any other relatively high density matrix may be employed in the preparation of the bolus. Exemplary of such prior art practices are U.S. Pat. No. 3,507,952 and U.S. Pat. No. 4,564,363.

European Patent Application 0,164,927 discloses a release device for ruminants comprising a succession of annular medicament containing segments contained in a liquid impermeable casing exposed at one end. The segments are penetrated by a rod of degradable material such as magnesium alloy. The rate of administration or bioavailability of each segment depends on the speed of degradation of the magnesium rod.

A major problem associated with the use of boluses in animals is the frequency that the boluses must be administered and the increase labor required to continually administer these boluses to the animal. Further, most ruminants such as cattle, sheep or goats are grazing animals which are prone to wander over vast areas of land for an extended period of time, thus making repeat administration of these boluses to the animals extremely difficult and economically unfeasible.

DESCRIPTION OF THE INVENTION

This invention comprises a veterinary dosage form that can deliver three or more doses of medicament intermittently at a preset time interval in the rumen from a single oral administration. No medicament is bioavailable in the interim period. This achieves a repeat action of the medicament by periodic release of dosage units in the rumeno reticular sac of ruminants rather than a single sustained release of medicament as known to the art. This also allows an effective treatment to be spread over a longer time span per space of dosage unit than the sustained release products.

The dosage form in accordance with this invention comprises a polymeric coated bolus containing a therapeutically active substance combined with excipients and a disintegrant in one section, and a separate weighted section which contains a material dense and heavy enough to permit the bolus to lodge in the rumeno-reticular sac of an animal. In a preferred embodiment, the composition comprises multi bolus units as described above, arranged in a layered configuration. Each bolus is joined together with a water soluble adhesive. The time it takes to release the therapeutically active substance in the separated boluses is dependent on the polymer coating, thickness of the coating and the amount of disintegrant in the formulation. The break time for the bolus ranges from about one week to 52 weeks, preferably from 2 to 25 weeks.

The polymeric coating material comprises a hydrophobic polymer that controls the delayed action of the basic bolus units. The polymer may be biodegradable or non biodegradable and is capable of fracturing under environmental stress and/or due to mechanical failure. Exemplary of biodegradable polymers that may be employed in this invention are poly(3-hydroxybutyrate) and copolymers, caprolactone polymers such as polycaprolactone and copolymers. Preferably, 3-hydroxybutyric acid is copolymerized with hydroxypentanoic acid and caprolactone is copolymerized with L lactide to form a poly($\epsilon$-caprolactone-co-L-lactide or polycaprolactone is blended with poly($\epsilon$-caprolactone-Co-L-lactide).

Further examples of biodegradable polymers that may be used in this invention are polylactides, polyglycolides, and copolymers of polylactides and polyglycolides; polyamides and copolymers of polyamides; polyesters; polyanhydries; poly(ortho esters); polyalkylcyanoacrylates; poly(alkyl glutamate); poly(methyl vinyl ether-maleic acid); and polyurethanes.

The above polymers undergo hydrolytic, oxidative or enzymatic degradation in the reticulum rumen environments at different rates.

Examples of non-biodegradable polymers that may be employed are cellulose esters, cellulose acetate butyrate, polyamides, polystyrene, and copolymers and polyurethanes. These polymers are brittle and can rupture under environmental stress. The delayed action is controlled by the mechanical strength and burst strength of the coated polymer film on aging. The thickness of the polymer coating ranges from about 0.1 mil to 20 mil, preferably from about 0.5 to 15 mil.

The therapeutically active substance may be any medicament or growth promotant which one desires to administer to ruminants such as cattle, sheep or goats in a controlled delayed release pattern. Most useful of the various ruminant active ingredients are anthelmintics such as albendazole, fenbendazole, oxfendazole, ivermectin, thiabendazole, mebendazole, cambendazole, morantel or levamisole; antibiotics such as streptomycin, virginiamycin, a vancomycin like glycopeptide, a tetracycline or an ionophore; and sulfa drugs such as sulfamethazine.

Exemplary of the dense materials which may be employed in the weighted section of the bolus are iron powder, sand, portland cement, plaster of paris, magnesium, oxychloride cement, calcium sulfate dihydrate, titanium oxide, barium sulfate iron oxide, clays, kaolin, zirconium oxide, glass, silicates, or mixtures thereof. The dense fillers may be present from about 5% to about 80% by weight of the total solids. Preferably, the filler will be present from about 25% to about 75% by weight of the total solids.

Most advantageously disintegrants will be employed in the bolus composition of this invention. They are particularly useful to control the extent of swelling of the bolus prior to the bursting of the polymer coating. Further, the disintegrant is also employed for the rapid release of the medicament in the rumen after the polymeric coating is ruptured. Exemplary of the disintegrants employed are starches, algins, gums, clays, celluloses, cation exchange resins, and preferably sodium starch glycolate. The disintegrating agent is present from about 0.50% to about 15%, preferably from about 2 to 8%.

Other excipients normally employed in the pharmaceutical art for tablet or bolus formulations designed for immediate or sustained release after oral administration may also be employed. These excipients may be, for example, fillers such as dicalcium phosphate, lactose or microcrystalline cellulose; binders such as gelatin, gums or sugars, lubricants such as talc, a metal stearate or cocoa butter or a granulating agent such as acacia tragacanth or gelatin.

When a water soluble adhesive is employed to join separate boluses, it may be for example, cellulose ethers, hydroxycellulose ethers, xanthan gum, starches, carrageenan, polyhydroxy-propyl- methylcellulose, gum arabic and gelatins. These compounds have film forming and adhesive characteristics and are applied in aqueous solutions on the basic bolus units.

The bolus can comprise many shapes such as, for example, cylindrical, oval, spherical, capsule or domed. Preferably, the size and shape should permit the bolus to be dispensed from a bolling gun. The finished bolus will weigh from about 5.0 grams to 50 grams and have a density of from 1.5 to 6.0 g/c.c. The preferred density is 2.0 to 4.0 g/c.c. Each bolus will have a length of from about 0.25 to 2.5 inches.

Although the main object of the invention is to produce a repeat action of the medicament by intermittent release of the boluses in the rumeno reticular sac, an intermittent sustained release of the medicament can also be easily obtained by anyone skilled in the art. For example, the medicament layer of the bolus can be in the form of sustained release granules, slugs or pellets. In this alternative intermittent sustained release bolus, sustained release material normally employed in the pharmaceutical art for a slow release tablet or bolus formulation may be employed. This material may be, for example, waxes, fatty acids, fatty alcohols, esters or an admixture thereof. The esters may be mono, di, or triglyceryl esters such as, for example, glyceryl monostearate, distearate or tristearate. The bolus would then also contain the same polymeric coatings as described hereinbefore to achieve the desired break time.

The multi bolus dosage form is orally administered to a ruminant and comes to rest in the reticulum rumen. The soluble adhesive dissolves or disintegrates rapidly in the ruminal fluid and each bolus unit separates from one another and remains at the bottom of the rumen. Each bolus will remain intact for a preset time according to the type and amount of polymeric coating used.

A detailed description and better understanding of this invention can be had by referring to the accompanying drawings which show a preferred embodiment of the present invention.

BRIEF DESCRIPTION OF THE DRAWINGS

FIG. 9 is a perspective view of a three stage bolus of this invention with the addition of an immediate release layer.

FIG. 10 is an enlarged fragmentary side elevational view taken on the line 10,10 of FIG. 9.

FIG. 11 is a graph illustrating the immediate release and the sequential pre set time delay operation of the 3 stage bolus illustrated in FIGS. 9 and 10.

DETAILED DESCRIPTION OF THE DRAWINGS

Figure 1:
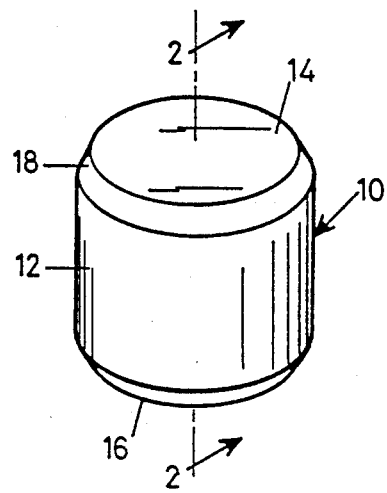
FIG. 1 is a perspective view of the bolus of this invention.
Figure 2:
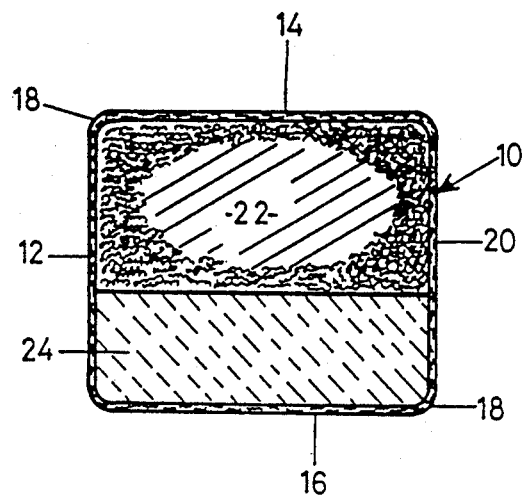
FIG. 2 is an enlarged sectional elevational view on the line 2,2 of FIG. 1 showing certain details of the bolus.

Referring to FIGS. 1 and 2 bolus 10 has a cylindrical body portion 12 and a planar top 14 and bottom 16 having rounded edges 18. The bolus contains a medicament layer 22 and a weighted layer 24 and is coated with a polymeric material 20.

Figure 3:
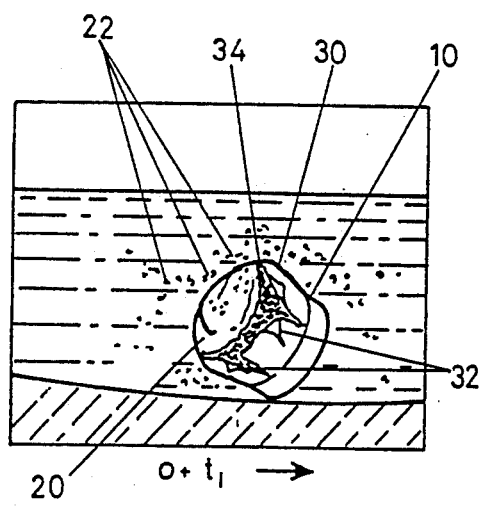
FIG. 3 is a semi schematic side elevational view partially in section illustrating the manner of operation of this invention for the delayed release of a medicament from the bolus shown in FIGS. 1 and 2.

FIG. 3 illustrates the manner in which the medicament is released from bolus 10 in the rumen. The bolus swells 30 which results in cracks 32 in the polymeric coating 20 to produce openings 34 through which the medicament 22 is released in the ruminal fluids.

Figure 4:
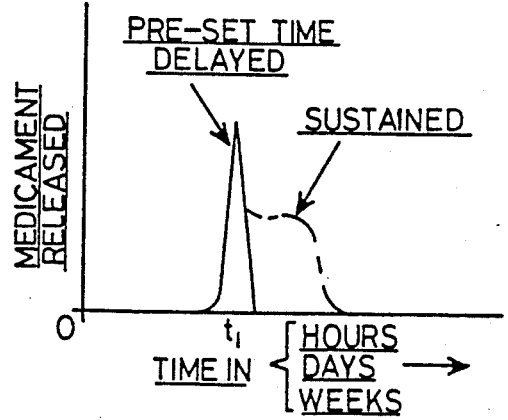
FIG. 4 is a graph illustrating the pre-set time delay and/or sustained release action of the bolus illustrated in FIGS. 1, 2 and 3.

The delayed release pattern for the medicament contained in the bolus of FIGS. 1, 2 and 3 is demonstrated in FIG. 4. The release may be a quick time delay or a sustained action depending on the composition of the medicament layer.

Figure 5:
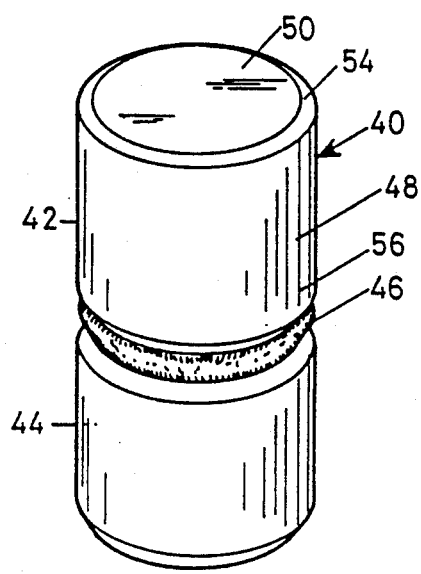
FIG. 5 is a perspective view of a two stage bolus of this invention.
Figure 6:
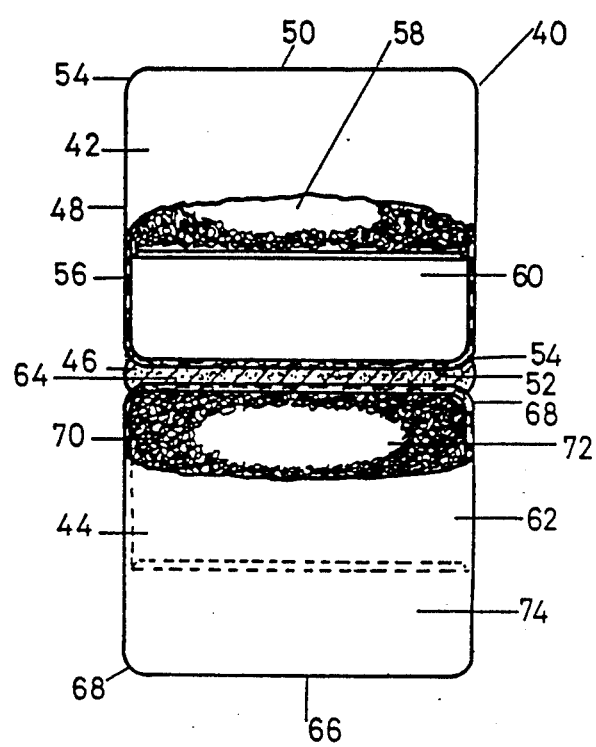
FIG. 6 is an enlarged side elevational view with portions broken away and in section of the two stage bolus shown in FIG. 5 illustrating certain details in construction.

FIGS. 5 and 6 represent a modification of the dosage form of FIG. 1 wherein two boluses are joined together in a layered configuration. The double bolus 40 has an upper bolus 42 joined to a lower bolus 44 by adhesive 46. The upper bolus 42 has a cylindrical body portion 48, a planar top 50 and bottom 52 and rounded edges 54. The upper bolus contains a medicament layer 58 and a weighted layer 60. The bolus has an outer polymeric coating 56. The lower bolus 44 has a cylindrical body portion 62 a planar top 64 and bottom 66 and rounded edges 68. The lower bolus has a medicament layer 72 and a weighted layer 74. A polymeric coating 70 having different release characteristics than the coating of the upper bolus surrounds the lower bolus. The different coatings permits each bolus to release the medicament intermittently.

Figure 7:
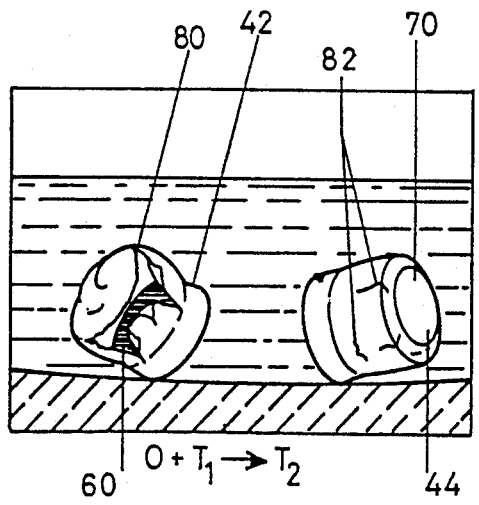
FIG. 7 is a semi schematic side elevational view with portions in section illustrating the manner of operation of a two stage bolus of this invention shown in FIGS. 5 and 6 for the sequential pre set time delayed release of medicament.

FIG. 7 demonstrates the double bolus of FIGS. 5 and 6 after being separated in the ruminal fluid. The upper bolus 42 is shown as having the medicament layer emptied and the swollen and cracked polymer shell 80 with the weighted layer 60 remaining. The lower bolus 44 remains intact due to the different characteristics of polymeric coating 70. The coating shows signs of cracking 82.

Figure 8:
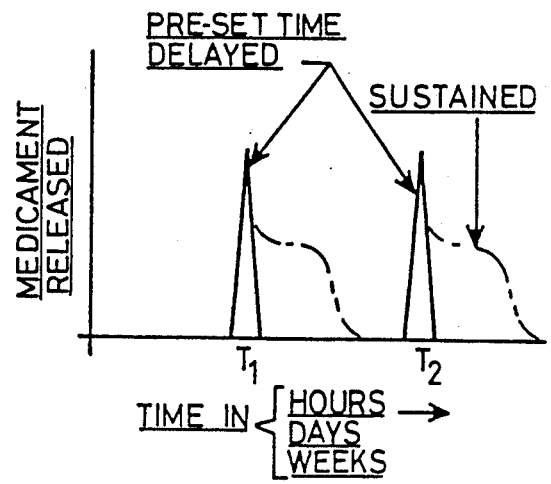
FIG. 8 is a graph illustrating the intermittent time delay and/or sustained release action of the two stage bolus shown in FIGS. 5, 6 and 7.

The intermittent delayed and sustained release profile of the medicament of the boluses of FIGS. 5, 6 and 7 is demonstrated in FIG. 8. $T_1$ represents the release of bolus 42 and $T_2$ represents the release characteristics bolus of 44.

A dosage form having an immediate release of the medicament together with intermittent delayed release characteristics is demonstrated in FIGS. 9 and 10. The four layered bolus 100 is represented by an immediate release medicament layer 102 which is coated with a water soluble adhesive coating 104. This layer is attached to a first bolus 106 having a cylindrical body portion 118, a planar top 120 and bottom 122 and rounded edges 124. The bolus also contains a medicament layer 13D, a weighted layer 128 and an outer polymeric coating 126. A second bolus 110 having polymeric coating 132 is attached to the first bolus with water soluble adhesive 108. The third bolus 114 having polymeric coating 134 is connected to the second bolus by an additional water soluble adhesive 116.

Each bolus as represented in the dosage forms of FIGS. 9 and 10 has a different polymeric coating composition which permits for the intermittent release of the medicament. The release pattern is illustrated in FIG. 11. The top medicament layer 102 which does not have a polymeric coating is released immediately. $T_1$ represents the release characteristics of bolus 106, $T_2$ of bolus 110 and $T_3$ of bolus 114.

The invention will be further clarified by the following specific examples. These examples are not limiting but are used to make obvious to one skilled in the art the full practice of this invention. For example, the coatings may be applied to the boluses in a variety of ways, i.e., dipping or spray coating. Multilayer rotary tablet machines employed to prepare layered tablets or boluses are well known to the art.

EXAMPLE 1

| Ingredients | Grams/Bolus |
|---|---|
| A - Medicated Layer | |
| Dicalcium phosphate | 8.78 |
| Albendazole | 3.00 |
| Sodium starch glycolate | 0.37 |
| Magnesium stearate | 0.12 |
| B - Weighted Layer | |
| Iron powder | 8.00 |
| Dicalcium phosphate | 4.00 |
| Magnesium stearate | 0.12 |
| | Grams |
| C-Homopolymer | |
| Poly(3-hydroxybutyrate) molecular weight 848,000 | 1.0 |
| Methylene chloride | 49.5 |
| 1,1,1-trichloroethane | 49.5 |
| | 100.0 |
| D - Homopolymer | |
| Poly(3-hydroxybutyrate), molecular weight 848,000 | 2.0 |
| Methylene chloride | 49.0 |
| 1,1,1-trichloroethane | 49.0 |
| | 100.0 |
| E - Copolymer | |
| Poly(3-hydroxybutyrate-co-poly-3-hydroxypentanoate) 83/17 monomer ratio, molecular weight 950,000 | 1.0 |
| Methylene chloride | 49.5 |
| 1,1,1-trichloroethane | 49.5 |
| | 100.0 |
| F - Copolymer | |
| Poly(3-hydroxybutyrate-co-poly-3-hydroxypentanoate) 83/17 monomer ratio, molecular weight 950,000 | 2.0 |
| Methylene chloride | 49.0 |
| 1,1,1-trichloroethane | 49.0 |
| | 100.0 |
| G - Water Soluble Adhesive | |
| Polyhydroxypropyl methylcellulose E4M | 5.0 |
| Deionized water | 95.0 |
| | 100.0 |

Ingredients "B" for the weighted layer were mixed and placed in the cavity of a 1-inch die. The powder was lightly compressed into a bolus with a 1-inch punch on a Carver press (Model C) at 3000 to 5000 PSI.

Ingredients "A" for the medicated layer were mixed and placed in the cavity of a 1-inch die on top of the compressed weighted layer. The medicated and weighted layer were compressed together with the 1-inch punch at 15,000 PSI. A spindle was attached to the bottom of the weighted layer.

Polymer coatings "C" and "D" were prepared by dissolving the polyhydroxybutyrate homopolymer in the solvents. By means of the spindle, the layered bolus was dipped into polymer solution C. The bolus was removed from the solution and the coating air dried. The coated bolus was then dipped in polymer solution "D", removed and air dried. The dip coating and air drying procedures were repeated until a coating thickness of approximately 5.0 mil was obtained. The bolus was then air dried for twenty four hours followed by drying for several hours in a 40° C. convection oven. The spindle wa then removed.

A second layered bolus was prepared as disclosed above. Polymer solutions "E" and "F" were prepared by dissolving the copolymer of poly(3-hydroxybutyrate) in the appropriate solvents. The bolus was then dip coated in the same fashion as the first bolus. The coating thickness was about 6.0 mils.

The soluble adhesive "G" was prepared by dissolving the polyhydroxypropyl methylcellulose in deionized water. The adhesive was applied to the bottom of the bolus 1 and the top of bolus 2. The two boluses were firmly pressed together and permitted to stand until the adhesive was dried and the two coated boluses were firmly adhered together.

EXAMPLE 2

Following the procedure of Example 1, employing the same ingredients, three two layered boluses were prepared. The boluses were coated as follows:

Bolus 1 was dip coated with copolymer poly (ε-caprolactone-co-L-lactide) a 25/75 monomer ratio, molecular weight of 44,000, having a thickness of 4.0–4.5 mils.

Bolus 2 was coated with a 1:1 blend of poly (ε-caprolactone) and poly (ε-caprolactone-co-L-lactide) 25/75 having a coating thickness of 5.5 mils.

Bolus 3 was coated with poly(ε caprolactone), molecular weight of 160,000 to a thickness of 4.5–5.0 mils.

The separate boluses were joined together with a water soluble adhesive solution of 10% pregelatinized starch in deionized water.

The separate boluses of Examples 1 and 2 were tested in the rumen of fistulated cattle (steers) with the following results:

Results of the In Vivo Test in the Rumen

| Bolus | Polymer Coating | Coating Thickness (mils) | Break Time of Coating (Days) |
|---|---|---|---|
| | Example 1 | | |
| 1 | Poly(3-hydroxybutyrate), m.w. 848,000 | 4.5–5.0 | 18–33 |
| 2 | Poly(3-hydroxybutyrate-co-poly-3-hydroxy-pentanoate), m.w. 950,000 | 4.5–6.5 | 48–108 |
| | Example 2 | | |
| 1 | Poly($\epsilon$-caprolactone-co-L-lactide), 25/75 monomer ratio, m.w. 44,000 | 4.0–4.5 | 10–11 |
| 2 | 1:1 Blend of Poly($\epsilon$-caprolactone) m.w. 160,000 and poly($\epsilon$-caprolactone-co-L-lactide) 25/75 m.w. 44,000 | 5.0–6.0 | 16 |
| 3 | Poly($\epsilon$-caprolactone), m.w. 160,000 | 4.5–5.0 | 21–28 |

What is claimed is:

1. A delayed release dosage form for ruminants capable of delivering a dose of a medicament to the rumen which comprises a single bolus containing a medicament dispersed in a filler and a second weighted layer containing a dense filler matrix which permits the bolus to lodge in the rumen, said bolus having a hydrophobic polymeric coating.

2. The dosage form according to claim 1 wherein the polymeric coating is a non-biodegradable polymeric coating selected from cellulose ester, cellulose acetate butyrate, polyamide, polystyrene and copolymers thereof, and polyurethane.

3. The dosage form according to claim 2 wherein the polymeric coating has a thickness of 0.1 to 20 mils.

4. The dosage form according to claim 1 wherein the polymeric coating is selected from poly(3-hydroxybutyrate), polycaprolactone, polylactide, polyglycolide, polyamide, polyester, polyanhydride, poly(ortho)ester, polyalkylcyanoacrylate, poly(alkylglutamate), poly(-methylvinyl ether-maleic acid), or polyurethane, and co-polymers thereof.

5. The dosage form of claim 1 wherein the dense filler matrix is iron powder.

6. The dosage form of claim 1 wherein a disintegrant is present in the medicament layer.

7. The dosage form of claim 6 wherein the disintegrant is sodium starch glycolate.

* * * * *